United States Patent [19]

Tamura et al.

[11] Patent Number: 4,849,351
[45] Date of Patent: Jul. 18, 1989

[54] **MULTIPLE READING FRAME *ESCHERICHIA COLI* EXPRESSION VECTORS**

[75] Inventors: Gakuzo Tamura, 2-17-12 Sanno, Ohta-ku, Tokyo; Koji Yoda; Yasuhiro Kikuchi, both of Tokyo; Makari Yamasaki, Koganei, all of Japan

[73] Assignee: Gakuzo Tamura, Tokyo, Japan

[21] Appl. No.: 939,230

[22] Filed: Dec. 8, 1986

Related U.S. Application Data

[63] Continuation of Ser. No. 796,535, Nov. 12, 1985, abandoned, which is a continuation of Ser. No. 526,493, Aug. 25, 1983, abandoned.

[30] Foreign Application Priority Data

Aug. 27, 1982 [JP] Japan ................. 57-147726

[51] Int. Cl.$^4$ ............... C12P 21/00; C12N 15/00; C12N 1/20; C12N 1/00
[52] U.S. Cl. .................... 435/68; 435/172.3; 435/320; 435/252.33; 435/70; 935/27; 935/29; 935/41; 935/48
[58] Field of Search ............ 435/68, 70, 172.3, 320, 435/253, 194; 935/27, 29, 41, 48

[56] References Cited

U.S. PATENT DOCUMENTS 4,375,514  3/1983  Siewert et al. ............ 435/172.3

FOREIGN PATENT DOCUMENTS 2071671  9/1981  United Kingdom .

OTHER PUBLICATIONS

Yoda et al, 1980, "Cloning of the Structural Gene of Alkaline Phosphatase of *E. coli* K12", *Agric. Biol. Chem.*, v. 44(5), 1213-1214.
Kikuchi et al, 1981, "Sequence of the Signal Peptide of *E. coli* Alkaline Phosphatase", Agric. Biol. Chem., v. 45(10), 2401-2402.
Kikuchi et al, 1981, "The Nucleotide Sequence of the Promoter and the Amino-Terminal Region of Alkaline Phosphatase Structural Gene . . . ", *Nucleic Acids Res.*, v. 9, 5671-5678.

*Primary Examiner*—Robin Teskin
*Attorney, Agent, or Firm*—Fitzpatrick, Cella, Harper & Scinto

[57] ABSTRACT

Vector plasmids are constructed to provide sites for insertion of a structural gene in phase with three reading frames downstream from the promoter of alkaline phosphatase gene of *Escherichia coli*.

3 Claims, 8 Drawing Sheets

3.14 Kb Iso-VECTORS

FRACTIONATION OF phoA'-lac'Z PROTEIN (7.5% SDS/PAGE)

MULTIPLE READING FRAME ESCHERICHIA COLI EXPRESSION VECTORS

This application is a continuation of application Ser. No. 796,535, filed Nov. 12, 1985, now abandoned, which is a continuation of application Ser. No. 526,493, filed Aug. 25, 1983, now abandoned.

BACKGROUND OF THE INVENTION

The present invention pertains to a novel vector and more particularly to vectors having an insertion site in phase with three reading frames downstream of the promoter of alkaline phosphatase gene (phoA) of *Escherichia coli*. In order to produce foreign proteins extracellularly by recombinant DNA technology, the present inventors have cloned DNA fragments containing the promoter sequence, the Shine-Dalgarno sequence (SD sequence) and the signal sequence of phoA and determined its base sequence. Thus it became possible to strongly express a desired polypeptide by linking a gene coding for desired peptides downstream from the phoA promoter. Also a method for excreting a desired peptide or polypeptide was provided by linking a gene coding for the peptide or polypeptide in phase with the signal sequence of phoA by adjusting the reading frame as is described in U.S. Patent Application Ser. No. 435,456, now abandoned, filed Oct. 20, 1982.

Many restriction sites became available for insertion of a desired gene as the result of the determination of the base sequence and the construction of the restriction map of the phoA fragment. Nevertheless, improvements to the phoA expression vector were considered desirable. To this end, versatile expression vectors have now been constructed which have insertion sites cleavable with common restriction enzymes and which are in phase with any of the three reading frames of an inserted gene.

SUMMARY OF THE INVENTION

The present invention provides a group of novel vectors having insertion sites in phase with three reading frames downstream from the phoA promoter of *Escherichia coli*.

The expression vector of the present invention can be prepared by introducing insertion sites in phase with the three reading frames at a restriction site downstream from the phoA promoter of *Escherichia coli*.

The following three positions are conceivable as insertion sites of a desired gene in the expression vector;
(1) a position just before the signal sequence;
(2) a position at the end of the signal sequence or at the 5'-terminal of alkaline phosphatase (APase) structural gene; and
(3) a position in the structural gene of APase.

The second position is considered to be most suitable for extracellular production of a large amount of foreign protein, but the other positions can also be used as insertion sites after appropriate modification to those described hereinafter.

BRIEF DESCRIPTION OF THE DRAWINGS

In the accompanying drawings.

DETAILED DESCRIPTION OF THE INVENTION

Figure 1:
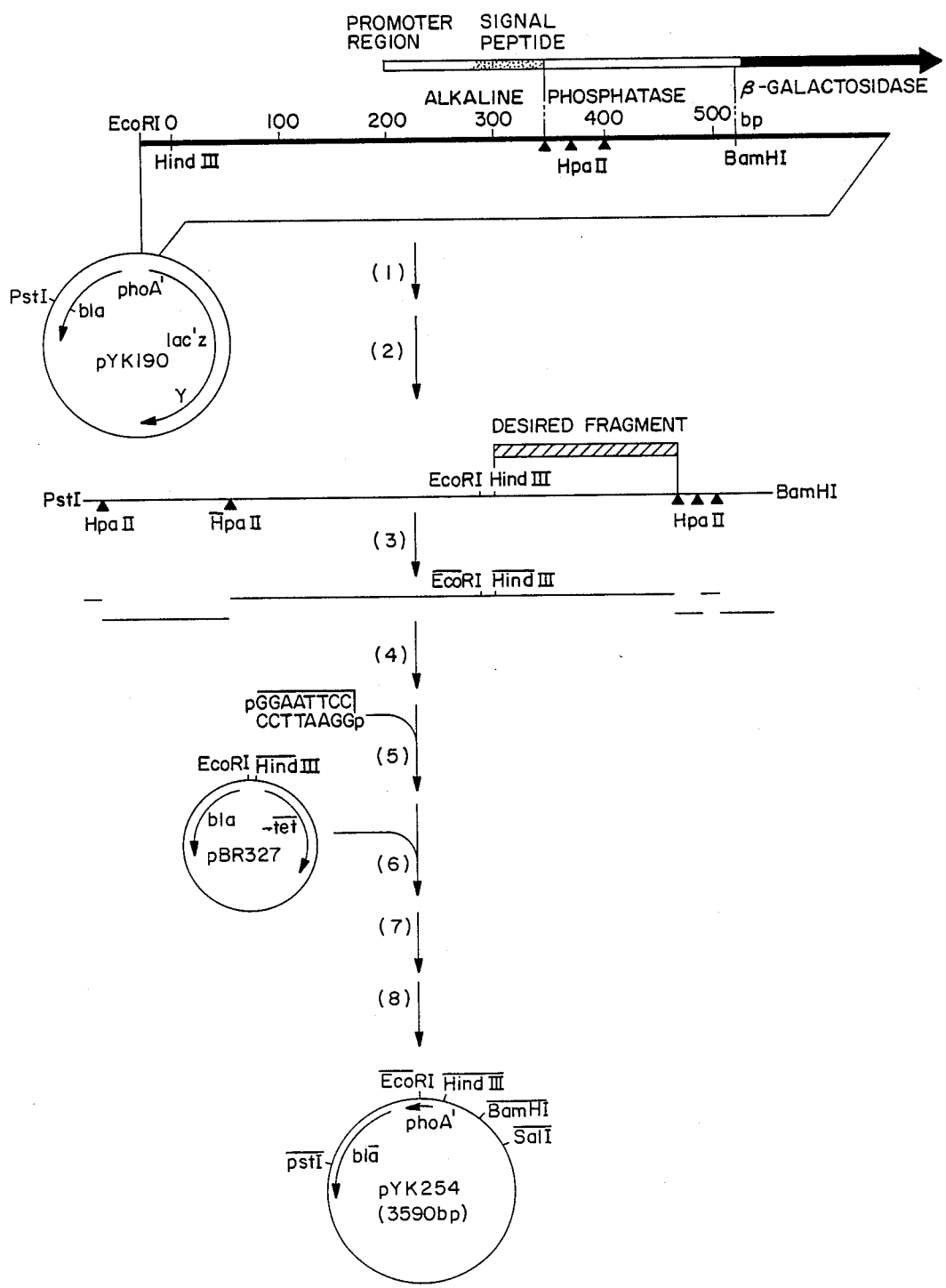
FIG. 1 illustrates the construction of pYK254, wherein (1) shows the step of cleavage with PstI and BamHI, (2) the step of separation of a 1.3 Kb fragment by agarose gel electrophoresis, (3) the step of cleavage with HpaII, (4) the step of filling-in of the sticky ends with PolI, (5) the step of ligating the EcoRI linker with T4 ligase, (6) the step of cleavage with HindIII and EcoRI, (7) the step of ligation with T4 ligase, and (8) the step of transformation of *Escherichia coli* MC1061.

As a site for insertion of a desired gene, usually an inherent restriction site downstream from a promoter to be used, or a restriction site construed by linking an appropriate linker at an inherent restriction site can be used. The linker is usually selected on the basis that its restriction site does not exist in the structural gene of a desired protein and/or in other parts of the vector, and its restricted termini are complementary to the cohesive ends of a desired gene.

For the cloning of a desired gene to express and secrete the desired protein under the control of the phoA promoter of *Escherichia coli*, it is most convenient to use the HpaII site between the triplet coding for the alanine of the last amino acid of the signal peptide and that for the arginine of the first amino acid of a sub-unit of mature alkaline phosphatase isoenzyme iso-1, as described above.

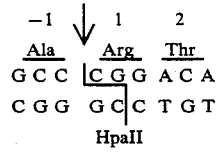

Although it is possible to use the HpaII site for cloning without any modification, it is more convenient to insert, at the HpaII site, a synthetic linker having common restriction sites such as AluI, BamHI, BclI, BglII, CfoI, ClaI(TaqI), EcoRI, FnuDII, HaeIII, HhaI, HindIII, HpaI, HpaII, HpcII(MspI), KpnI, MspI, PstI, SacI, SalI, SmaI(XamI), SstI, ThaI, XbaI, XhoI(TaqI, AvaI), or the like.

The synthetic linker can be attached, for example, in the following manner:

A DNA fragment containing the promoter - signal region of phoA which has been cloned in, for example, pYK190 (see U.S. patent application Ser. No. 435,456, filed Oct. 20, 1982, now abandoned, can be cut out by an appropriate restriction enzyme. A DNA fragment of about 1.3 Kbp is isolated by double digestion with PstI and BamHI and agarose gel electrophoresis. After the isolation, the fragment is digested with HpaII under appropriate conditions, and the reaction is stopped by heating. The reaction mixture is allowed to react with deoxyadenosine triphosphate (hereinafter referred to as dATP), deoxyguanosine triphosphate (hereinafter referred to as dGTP), deoxycytidine triphosphate (hereinafter referred to as dCTP), deoxythymidine triphosphate (hereinafter referred to as dTTP) and DNA polymerase I of *Escherichia coli* to fill in. Then, ethanol is added to the reaction mixture to recover DNA as precipitates.

Then, a preferable linker, for example, EcoRI, HindIII or BamHI linker, or the like is ligated with the filled-in ends of DNA cut with HpaII restriction enzyme. For example, in the case of EcoRI linker, the 5' terminal of the linker is phosphorylated with daTP and T4 polynucleotide kinase in advance, and the phosphorylated linker is attached to both ends of the said HpaII fragment through blunt end ligation with T4 DNA ligase. The ligation reaction is carried out in the presence of 1-50 mM Tris-HCl (pH 7-8), 1-50 mM MgCl$_2$, 1-20 mM dithiothreitol and 0.1-2 mM ATP at 4°-20° C. for 1-20 hours. Then, ethanol is added to recover DNA as precipitates.

Then, the recovered DNA and plasmid pBR327 [Gene 13, 25-35 (1981), Luis Covarrubias et al] are double digested with HindIII and EcoRI. The reaction is carried out in the buffer solution for HindIII at 30°-37° C. for 1-3 hours. The reaction is stopped by heating.

Then, the HindIII - EcoRI reaction mixture is mixed with 5-10 mM dithiothreitol and 0.1-1 mM ATP and subjected to ligation reaction at 4°-20° C. for 1-20 hours with T4 DNA ligase. After the ligation reaction, appropriate strains of Escherichia coli are transformed with the reaction mixture, and ampicillin - resistant (Ap$^R$) strains are selected on a bouillon medium containing ampicillin. The transformation is carried out according to the method of Mandel and Higa [J. Mol. Biol. 53 159 (1970), see Idenshi Sosa Jikkenho (Experimental Procedure for Gene Engineering), ed. by Yasuyuki Takagi, Kodansha Publishing Co. (1980)].

The thus obtained Ap$^R$ strains are smeared on a bouillon medium containing tetracycline (Tc) to test Tc sensitivity, and Tc - sensitive (Tc$^S$) strains are retained. Plasmid pYK254 possessed by one of the strains has the restriction map shown in FIG. 1, and has been thus confirmed to have the desired structure.

To change the direction of the promoter of phoA inserted in pBR327 for convenience of successive operations, plasmid pYK254 is double digested with EcoRI and HincII, and a fragment of 971 bp containing the promoter of phoA is isolated by agarose gel electrophoresis. The double digestion is carred out, for example, in 1-50 mM Tris-HCl (pH 7-8.5), 1-20 mM MgCl$_2$, 1-20 mM 2-mercaptoethanol and 1-100 mM NaCl at 30°-37° C. for 1-3 hours.

Figure 2:
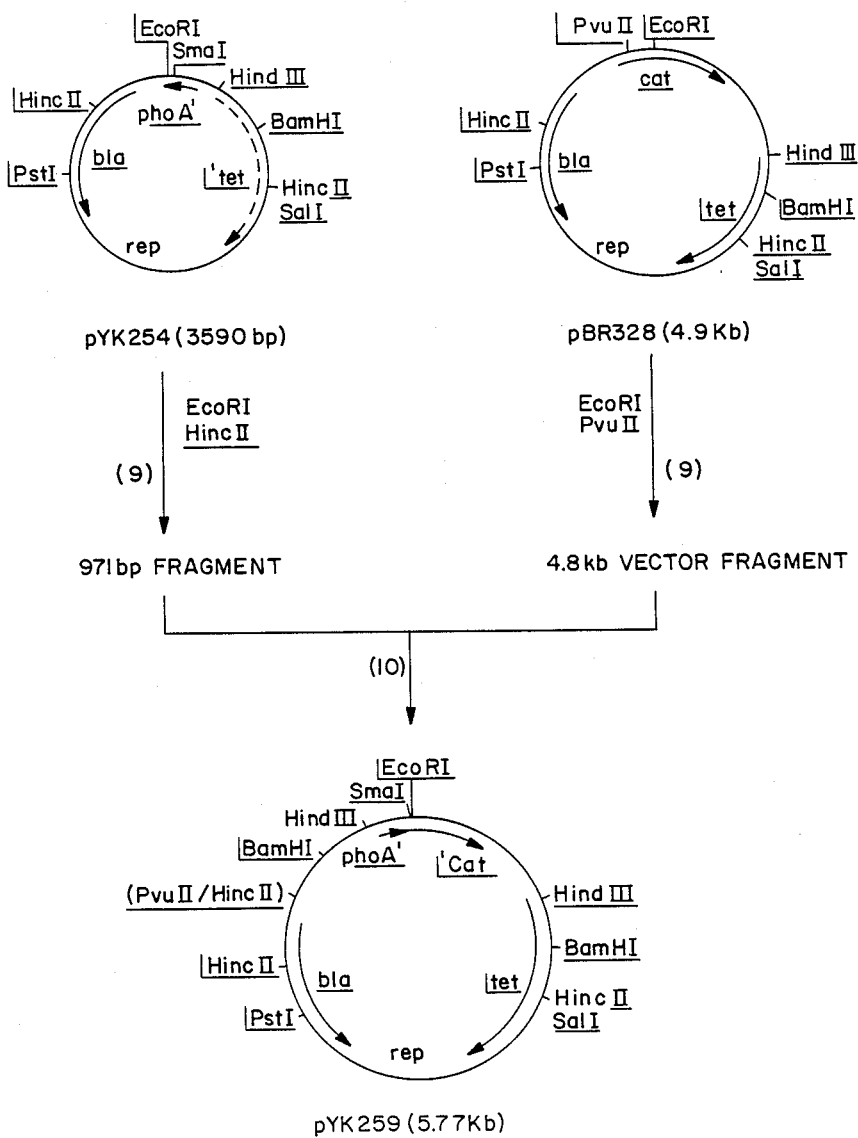
FIG. 2 illustrates the construction of pYK259, wherein (9) shows separation by agarose gel, and (10) ligation with T4 ligase.

Separately, plasmid pBR328 [Gene 13 25-35 (1981), Luis Covarrubias et al] is double digested with EcoRI and PvuII. The reaction is carried out, for example in 1-50 mM Tris-HCl (pH 7-8), 1-20 mM MgCl$_2$, 10-100 mM NaCl, and 1-20 mM 2-mercaptoethanol at 30°-37°C. for 1-4 hours. The larger fragment (4.8 Kb) of pBR328 is isolated by agarose gel electrophoresis and ligated to the 971 bp fragment with T4 DNA ligase. Then strains of Escherichia coli are transformed with the ligation mixture, and Ap$^R$ strains are selected on a bouillon medium containing ampicillin. Then, Tc and chloramphenicol (Cm) sensitivities of the thus obtained Ap$^R$ strains are tested to select Ap$^R$ Tc$^R$ Cm$^S$ (Cm - sensitive) strains. Plasmid pYK259 possessed by one of the thus obtained Ap$^R$ Tc$^R$ Cm$^S$ strains has the desired structure as shown in FIG. 2.

Plasmids with different reading frame are constituted as follows:

(1) Formation of the reading frame "1":

pYK259 is digested with SmaI. The reaction is carried out, for example, in the presence of 1-50 mM Tris-HCl (pH 7-8.5), 1-20 mM MgCl$_2$, 5-50 mM KCl, and 1-20 mM 2-mercaptoethanol at 30°-37° C. for 1-4 hours. The reaction is stopped by heating, and the plasmid is then digested with AvaI. The reaction is carried out, for example, in the presence of 10-20 mM Tris-HCl (pH 7.4), 2.5-25 mM MgCl$_2$, and 20-50 mM NaCl at 30°-37° C. for 1-3 hours. The reaction is stopped by heating, and then the plasmid is subjected to fill-in reaction under the same conditions as above by DNA polymerase I of *Escherichia coli*. Ethanol is added to recover DNA as precipitates.

Phosphorylated EcoRI linker is ligated to both ends of the thus obtained DNA with T4 DNA ligase in the same manner as above. The reaction is stopped by heating, and after addition of NaCl, the reaction mixture is digested with EcoRI. The reaction is stopped by heating. The DNA is circularized with T4 DNA ligase, and *Escherichia coli* is transformed with the circular DNA. Then, AP$^R$ strains are selected.

Figure 3:
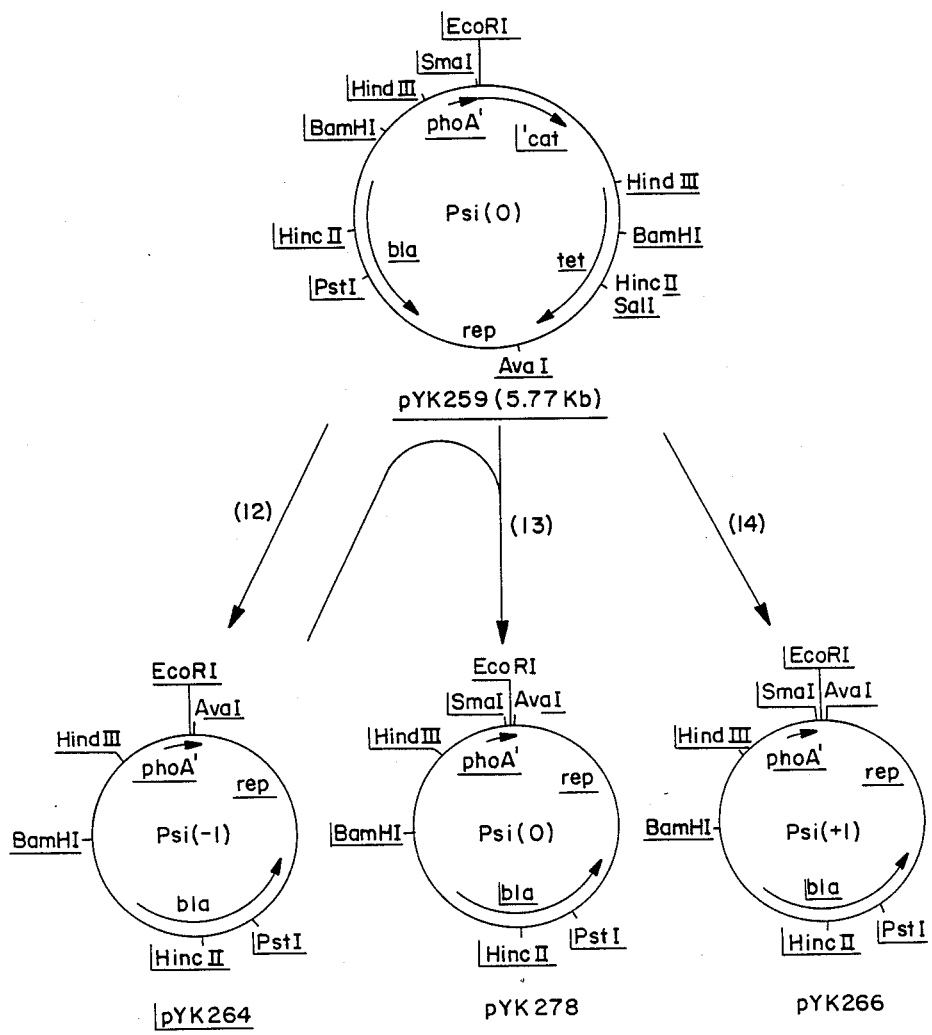
FIG. 3 illustrates the change of reading frames, wherein (12) shows a process of digestion with SmaI, (13) the exchange of EcoRI - PstI fragments, and (14) a process of digestion with AvaI.

It has been found that at least one of the Ap$^R$ strains contains a plasmid having the desired restriction map shown in FIG. 3. The base sequence in the junction is shown below, and the plasmid is named pYK264.

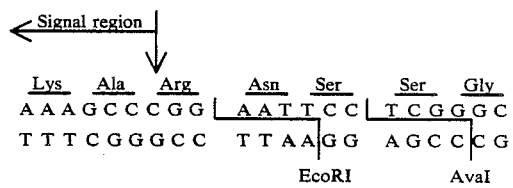

(2) Formation of the reading frame "0":

pYK264 is double digested with EcoRI and PstI, and the smaller fragment (1.10 Kbp) is isolated by agarose gel electrophoresis. The double digestion is carried out in the presence of 20-100 mM Tris-HCl (pH 7.4), 5-7 mM MgCl$_2$ and 50-60 mM NaCl at 30°-37° C. for 1-3 hours.

Likewise, pYK259 is double digested with EcoRI and PstI to obtain the smaller fragment (2.04 Kbp).

These two fragments are ligated with T4 DNA ligase in a ligation buffer solution at 4°-15° C. for 3-20 hours.

Strains of *Escherichia coli* are transformed with the reaction mixture to obtain Ap$^R$ strains, one of which has the plasmid with the structure as shown in FIG. 3. The base sequence in the junction is given below where an additional "G" is inserted compared to the base sequence of pYK264:

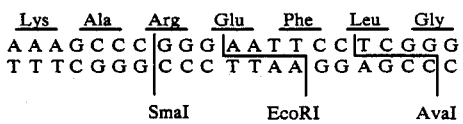

(3) Formation of the reading frame "+1":

pYK259 is digested with restriction enzyme AvaI under the same conditions as above. The reaction is stopped by heating, and the fill-in reaction is also carried out under the same conditions as above with DNA polymerase I of *Escherichia coli*. Then, ethanol is added to recover DNA as precipitates.

EcoRI linker is attached to both sides of the thus obtained DNA with T4 DNA ligase. The DNA with EcoRI linker is treated with EcoRI restriction enzyme to expose cohesive ends and then circularized with T4 DNA ligase. The foregoing operations are carried out in the same manner as above.

*Escherichia coli* is transformed with the circular plasmid DNA to obtain $Ap^R$ strains, one of which has the plasmid with the structure as shown in FIG. 3. The sequence of the junction is given below, where two additional "G" s are inserted compared to the structure of pYK264:

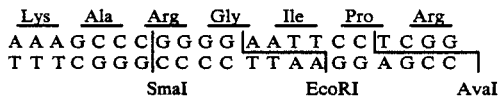

As described above, cloning vectors having an EcoRI site and an AvaI site as cloning sites and having the three reading frames can be prepared.

Linkers other than EcoRI linker can be inserted into the HpaII site, and a cloning vector having three reading frames can be prepared in the same manner as above. Furthermore, it is also possible to prepare a derivative having a different cloning site from pYK264, 278 and 266 (hereinafter referred to as Psi iso-vectors). For example, when these Psi iso-vectors are double digested with EcoRI and PstI, and a fragment containing the promoter of phoA' (2.04 Kbp) is ligated to the larger fragment (9.16 Kbp) of plasmid pMC1403 double-digested in the same manner as above, a group of vectors having a BamHI cloning site corresponding to three reading frames is formed.

Figure 5:
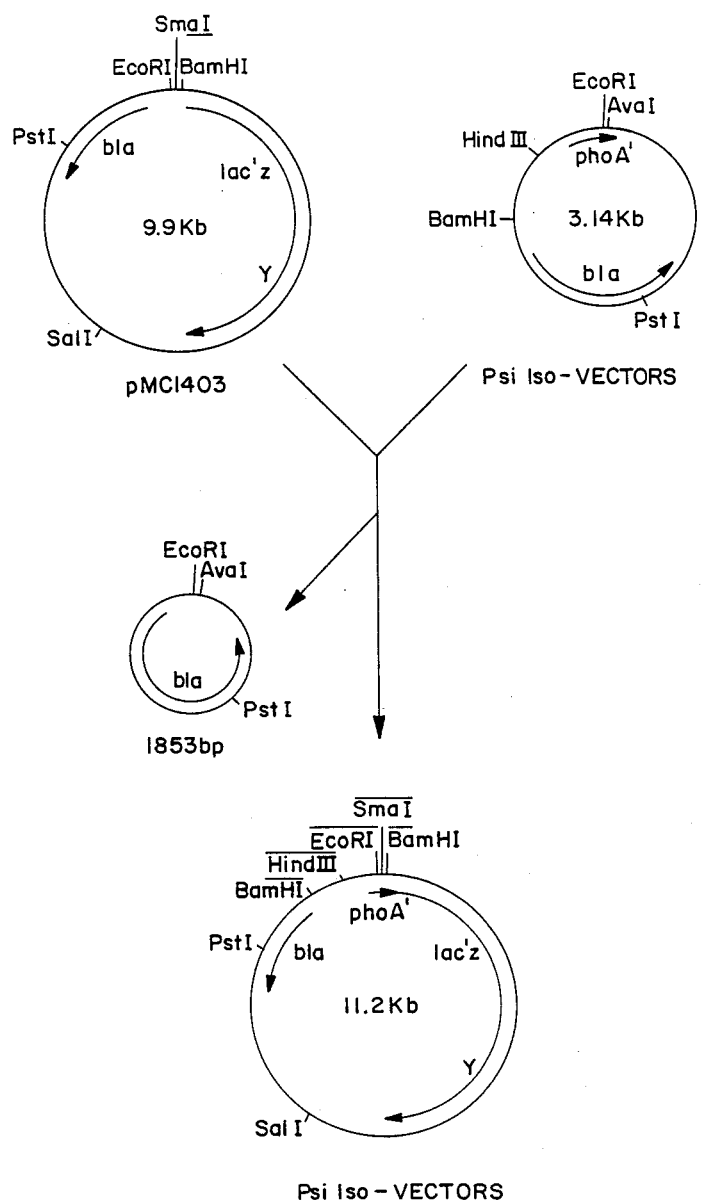
FIG. 5 illustrates the exchange of EcoRI - PstI fragments.
Figure 6:
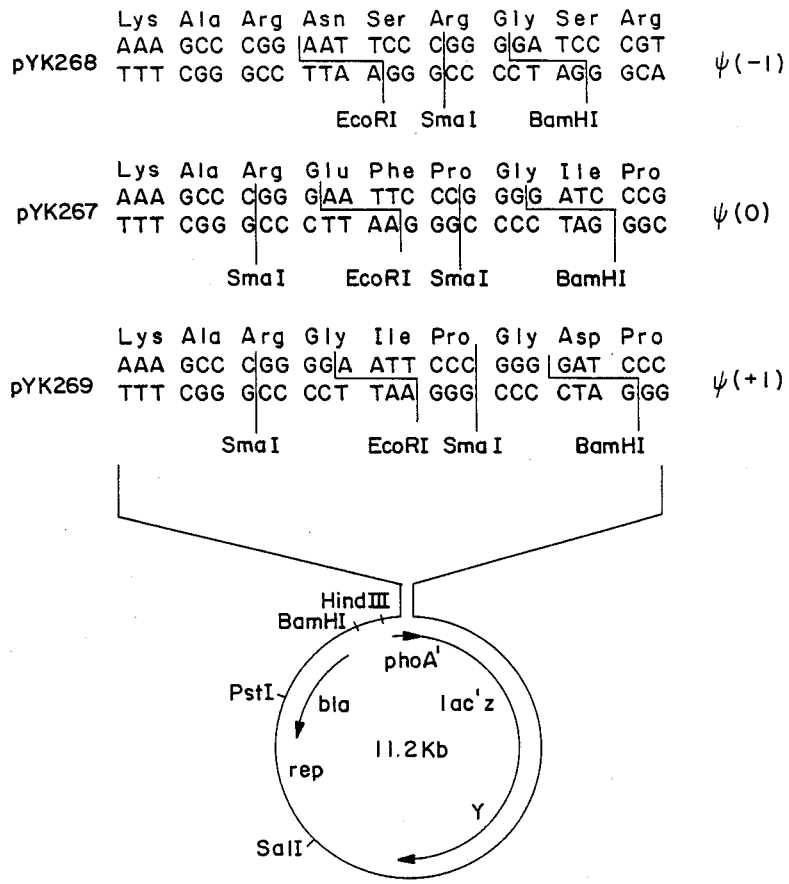
FIG. 6 illustrates the restriction map and sequence of cloning sites of Psi iso-vectors pYK268, pYK267 and pYK269.

The procedure is described below:

Plasmid pMC1403 [M. Casadaban et al J. Bacteriol. 143 971–980 (1980)] is double digested with PstI and EcoRI, and the larger fragment (9.16 Kbp) is isolated by agarose gel electrophoresis in the same manner as in the preparation of pYK278. Likewise, Psi iso-vectors are double digested with EcoRI and PstI, and the larger fragment (2.04 Kbp) is isolated by agarose gel electrophoresis. These fragments are linked together in a ligation buffer solution with T4 DNA ligase. *Escherichia coli* is transformed with the thus obtained plasmid, and $Ap^R$ strains are selected on a bouillon plate containing ampicillin. The $Ap^R$ strains are examined for a plasmid having the desired size and structure. The process is outlined in FIG. 5. In this manner, pYK268 is obtained from pYK264 and pMC1403, pYK267 from pYK278 and pMC1403, and pYK269 from pYK266 and pMC1403. The base sequence in the junction between the two plasmids (pMC1403) and one of Psi iso-vectors) of these plasmids and restriction map of the plasmids are shown in FIG. 6. By this modification, the BamHI site can be added to Psi iso-vectors as a new cloning site.

The thus formed Psi iso-vectors pYK268, 267 and 269 all have lac Z gene (structural gene of β-galactosidase) lacking N-terminal 8 amino acids downstream from the promoter signal sequence of Apase. Since these vectors cover the three reading frames, one of the vectors must express β-galactosidase containing all or a part of amino acids in the signal peptide of phoA and amino acids coded by the linker in place of N-terminal 8 amino acids under the control of phosphate. The expression can be easily detected by the formation of blue lac+ colonies after transformers of lac− *Escherichia coli* are smeared and grown on agar plates of medium 121 containing 5-bromo, 4-chloro, 3-indolyl-D-galactoside (X-gal). Medium 121 contains 15 g of agar, 4 g of glucose, 4.68 g of sodium chloride, 1.5 g of potassium chloride, 1.08 g of ammonium chloride, 0.35 g of sodium sulfate, 0.2 g of magnesium chloride, 0.029 g of calcium chloride, 0.5 mg of ferric chloride, 0.27 mg of zinc chloride, and 12 g of trishydroxymethylaminomethane in 1 l, and is adjusted to pH 7.5 with hydrochloric acid. Furthermore, strains containing one of the plasmids pYK268, 267 and 269 are grown in medium 121 without agar, the cells were then harvested. Whole cell extracts prepared by sonic disintegration, by lysozyme treatment or by sodium dodecyl sulfate (SDS) treatment are subjected to SDS-polyacrylamide gel electrophoresis. A protein band of about $120 \times 10^3$ dalton is specifically detected in one of the extracts obtained from cells grown in the phosphate-depleted medium. This indicates that a protein with nearly the same size to β-galactosidase of *Escherichia coli* is expressed under the control of phosphate.

It is obvious from the foregoing that these vectors are useful in the cloning and expression of a desired gene.

Various expression vectors thus obtained all retain the signal sequence of APase and the triplet corresponding to the N-terminal arginine of sub-unit APase iso-1. When a desired gene is cloned at EcoRI, AvaI or BamHI site, the desired gene may be expressed as fused protein containing the signal peptide of APase and at least one arginine in addition to the desired protein. Since APase of *Escherichia coli* is processed (removal of signal peptide during secretion) at the amino group side of the arginine, it is highly probable that the expressed peptides encoded in a desired gene is secreted after the processing at the peptide bond between the carboxyl group of the last alanine in the signal peptide and the amino group of the N-terminal arginine of APase. In this sense, the vectors of the present invention can be called expression and secretion vectors.

Certain specific embodiments of the invention are described in the following representative examples.

EXAMPLE 1

In this example, plasmid pYK190 (U.S. Patent Application Ser. No. 435,456, now abandoned, was double digested with PstI (restriction enzyme of *Pseudomonas stuartii*, made by Takara Shuzo Co., Japan) and BamHI (restriction enzyme of *Bacillus amyloliquefaciens* H, made by Takara Shuzo Co., Japan) under the following conditions. At first, 20 μg of pYK190 was incubated with 40 units of PstI and 40 units of BamHI in the presence of 100 μl of 20 mM Tris-HCl (pH 7.4), 7 mM MgCl$_2$, 60 mM NaCl and 2mM 2-mercaptoethanol at 37° C. for one hour. The reaction was stopped by heating (70° C., 5 minutes), and the reaction mixture was subjected to agarose gel electrophoresis to isolate 1 μg of the 1.3 Kbp DNA fragment. The agarose gel electrophoresis was carried out with 1.0% agarose gel (20×15×0.5 cm) at 150 volts for 2 hours [buffer solution: 40 mM Tris-acetate (pH 7.8)], and staining was carried out with 0.5 μg/ml ethidium bromide for 5 to 10 minutes. After the staining, the 1.3 Kbp fragment was cut out under ultraviolet irradiation, and placed in a pyrex tube with an inner diameter of 5 mm. A dialysis membrane was attached to the lower end of the tube and the fragments were extracted by electrphoresis (5 mA/tube for one hour in the same buffer solution as above).

The resulting 1.3 Kpb DNA fragment was digested with two units of HpaII (restriction enzyme of Haemophilus parainfluenzae, made by Takara Shuzo Co., Japan) in the presence of 50 μl of 10 mM tris-HCl (pH 7.5), 7 mM MgCl$_2$ and 7 mM 2-mercaptoethanol at 37° C. for one hour. The reaction was stopped by heating at 70° C. for 5 minutes, and the reaction mixture was adjusted so as to contain 50 mM Tris-HCl (pH 7.8), 6.6 mM MgCl$_2$ and 1 mM 2-mercaptoethanol. 20 μM each of dATP, dGTP, dCTP and dTTP and one unit of DNA polymerase I of Escherichia coli (made by New England Biolabs) were added to the mixture to fill in the recessed 3' ends of the DNA at 30° C. for 60 minutes. Ethanol was added to the reaction mixture to recover, as precipitates, the DNA with filled-in HpaII termini.

The filled-in HpaII termini were linked with EcoRI linker under the following conditions. At first, 10 μg of EcoRI linker (made by Takara Shuzo Co., Japan) was phosphorylated with 100 μM ATP in the presence of 50 mM Tris-HCl (pH 7.6), 10 mM MgCl$_2$, 10 mM 2-mercaptoethanol and T4 polynucleotide kinase (made by Takara Shuzo Co., Japan). Then, about 0.2 μg of the phosphorylated EcoRI linker was ligated to both ends of the said DNA (with filled-in HpaII terminal) with T4 DNA ligase (made by New England Biolabs). The ligation reaction was carried out in the presence of 20 mM Tris-HCl (pH 7.6), 10 mM MgCl$_2$, 10 mM dithiothreitol and 0.5 mM ATP at 15° C. for 4 hours. Ethanol was then added to the reaction mixture to recover 0.7 μg of the DNA as precipitates.

Then, 0.7 μg of the recovered DNA and 2 μg of plasmid pBR327 [prepared according to the procedure disclosed in Gene 13 25–35 (19981)] were double digested with HindIII (restriction enzyme of Haemophilus influenzae, made by Takara Shuzo Co., Japan) and EcoRI [restriction enzyme of Escherichia coli RY 13, made by Takara Shuzo Co., Japan]. The reaction was carried out in a buffer solution for HindIII [20 mM Tris-HCl (pH 7.4), 7 mM MgCl$_2$ and 60 mM NaCl]containing 4 units each of the enzymes at 37° C. for one hour. The reaction was stopped by heating at 70° C. for 5 minutes. The reaction mixture was then mixed with 10 units of T4 DNA ligase, 10 mM dithiothreitol, and 0.5 mM ATP, and subjected to ligation at 15° C. for 4 hours. After ligation, Escherichia coli MC 1061 (Δlac Z) [Casadaban et al, J. Bacteriol. 143 911–980 (1980)] was transformed with the ligation mixture, and ampicillin resistant (Ap$^R$) strains were selected on bouillon medium containing 100 μg/ml ampicillin (Ap) (made by Eiken Kagaku Co., Japan). The transformation was carried out according to the method of Mandel and Higa [J. Mol. Biol. 53 159 (1970)]. The resulting Ap$^R$ strains were smeared on a bouillon medium containing 20 μg/ml tetracycline (Tc) to select tetracycline-sensitive (Tc$^S$) strains. Plasmid pYK254 possesed by one of the Ap$^R$Tc$^S$ strains has the restriction map shown in FIG. 1 and has been confirmed to have the desired structure.

Then, to change the direction of phoA promoter inserted in pBR 327 for convenience of the successive operation, pYK254 was double digested with EcoRI and HincII (restriction enzyme of Haemophilus influenzae RC, made by Takara Shuzo Co., Japan), and the 971 bp DNA fragment containing the phoA promoter was isolated therefrom by agarose gel electrophoresis. The double dispersion was carried out by incubating 4 μg of pYK254 with 8 units each of both restriction enzymes in the presence of 50 μl of 10 mM Tris-HCl (pH 8.0), 7 mM MgCl$_2$, 7 mM 2-mercaptoethanol and 60mM NaCl at 37° C. for one hour.

Separately, 1 μg of plasmid pBR328 [Gene 13 25–35 (1981)] was double digested with 2 units of each EcoRI and PvuII (restriction enzyme of Proteus vulgaris, made by Takara Shuzo Co., Japan). The reaction was carried out in the presence of 20 μl of 10 mM Tris-HCl (pH 7.5), 7 mM MgCl$_2$, 60 mM NaCl, and 7 mM 2-mercaptoethanol at 37° C. for one hour. The reaction was stopped by heating, and the larger fragment (4.8 Kbp) of double-digested pBR328 was isolated by agarose gel electrophoresis and then mixed with the previously isolated 971 bp fragment. They were ligated with T4 DNA ligase. Escherichia coli MC1061 was transformed with the ligated DNA and Ap$^R$ strains were selected on a bouillon plate containing 100 μg/ml ampicillin. By testing the sensitivity of the thus obtained Ap$^R$ strains to 20 μg/ml Tc and 25 μg/ml choramphenicol (Cm), Ap$^R$, Tc$^R$ and chloramphenicol sensitive (Cm$^S$) strains were selected. Plasmid pYK259 possessed by one of the thus obtained Ap$^R$Tc$^R$Cm$^S$ strains has the desired structure as shown in FIG. 2.

EXAMPLE 2

In this example, the change of pYK259 reading frame is carried out.

(1) Formation of pYK264 (reading frame "−1"):

At first, 1 μg of pYK259 was digested with 2 units of SmaI (restriction enzyme of Serratia marcescens, Sb, made by Takara Shuzo Co., Japan) in the presence of 20 μl of 10 mM Tris-HCl (pH 8.0), 7 mM MgCl$_2$, 20 mM KCl and 7 mM 2-mercaptoethanol at 37° C. for one hour. The reaction was stopped by heating at 70° C. for five minutes, and the reaction mixture was adjusted so as to contain 20 mM Tris-HCl, 10 mM MgCl$_2$ and 20 mM NaCl. Two units of AvaI (restriction enzyme of Anabaena variabilis, made by Bethesda Research Laboratories, which will be hereinafter referred to as BRL) ws then added to the reaction mixture and the reaction mixture was incubated at 37° C. for one hour. The reaction was stopped by heating at 70° C. for 5 minutes, and then the reaction mixture was subjected to fill-in reaction with one unit of DNA polymerase I of Escherichia coli under the same conditions as above. After the reaction, ethanol was added to recover DNA as precipitates.

Then, 0.1 μg of EcoRI linker phosphorylated in the same manner as above was ligated to both termini of the DNA with T4 DNA ligase in the same manner as above. The reaction was stopped by heating at 70° C. for 5 minutes. The reaction mixture was supplemented wiht NaCl so as to contain 50 mM NaCl, and the DNA with EcoRI linker was digested with EcoRI. The reaction was stopped by heating and the DNA digested with EcoRI was circularized with T4 DNA ligase.

*Escherichia coli* MC1061 was transformed with the circular DNA, and Ap$^R$ strains were selected.

Figure 4:
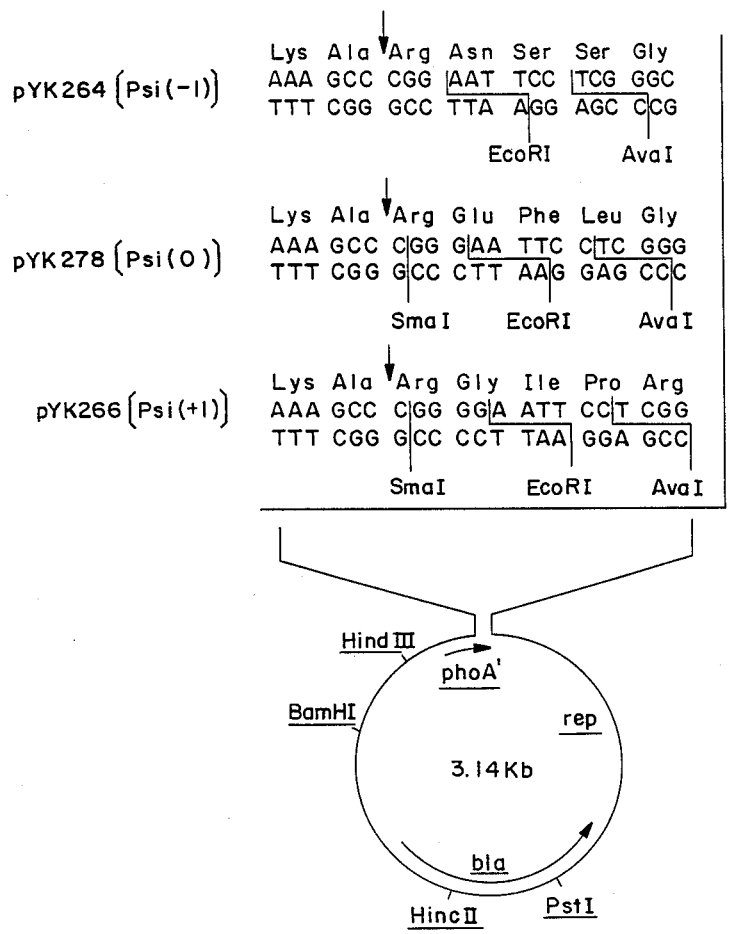
FIG. 4 illustrates the restriction map and sequence of cloning sites of Psi iso-vectors pYK264, pYK278 and pYK266.

Plasmid pYK264 possessed by one of the strains has the restriction enzyme map shown in FIG. 3, and the base sequence in the junction is shown in FIG. 4.

(2) Formation of pYK278 (reading frame ("0"):

One μg of pYK264 was double digested with 2 units each of EcoRI and PstI, and the smaller fragment (1.10 Kbp) was isolated by agarose gel electrophoresis. The double digestion was carried out in the presence of 20 μl of 20 mM Tris-HCl (pH 7.4), 7 mM MgCl$_2$ and 50 mM NaCl at 30° C. for 2 hours.

Likewise, 1 μg of pYK259 was digested with EcoRI and PstI to obtain the smaller fragment (2.04 Kbp).

These two fragments were ligated in a ligation buffer [20 mM Tris-HCl (pH 7.6), 10 mM MgCl$_2$, 10mM dithiothreitol and 0.5 mM ATP] with 0.1 unit of T4 DNA ligase at 15° C. for 4 hours. *Escherichia coli* MC1061 was transformed with the reaction mixture to obtain Ap$^R$ transformants.

Plasmid pYK278 possessed by one of the strains has the restriction enzyme map shown in FIG. 3, and the sequence of the junction is shown in FIG. 4, pYK278 has an additional "G" compared to pYK264.

(3) Formation of pYK266 (reading frame "+1"):

One μg of pYK259 was digested with 2 units of AvaI in the same manner as described above. The reaction was stopped by heating at 70° C. for 5 minutes, and the fill-in reaction was carried out with DNA polymerase I of *Escherichia coli* as described above. Then, ethanol was added to obtain DNA as precipitates.

In the same manner as in the construction of pYK264, EcoRI linker was attached to both termini of the filled-in AvaI fragment. It was then digested with EcoRI restriction enzyme and circularized with T4 DNA ligase. *Escherichia coli* MC1061 was transformed with the circular plasmid DNA to obtain Ap$^R$ transformants.

Plasmid pYK266 possessed by one of the strains has the restriction enzyme map shown in FIG. 3, and the sequence in the junction is shown in FIG. 4. pYK266 has two additional "G"s compared to pYK264.

Through (1) to (3), three cloning vectors having EcoRI and AvaI as cloning sites and corresponding to the three reading frames have been prepared. The strains containing pYK264, pYK278 and pYK266 have been deposited with the Fermentation Research Institute, Agency of Industrial Science and Technology, Japan as FERM P-6654, 6655 and 6656, respectively and have been transferred to the NRRL under the Budapest Treaty as NRRL B-15563, 15564 and 15565.

EXAMPLE 3

In this example, derivatives of pYK264, 278 and 266 are constructed.

One μg of plasmid pMC1403 [J. Bacteriol. 143 971–980 (1980)] was double digested with 2 units each of PstI and EcoRI as described in Example 2 (2), and the larger fragment (9.16 Kbp) was isolatd by agarose gel electrophoresis.

Separately, 1 μg of each of pYK264, 278 and 266 were also double digested with 2 units each of EcoRI and PstI, and the larger fragment (2.04 Kbp) was isolatd by agarose gel electrophoresis.

The 9.16 Kbp and 2.04 Kbp fragments were ligated with T4 DNA ligase under the same conditions as in Example 2. *Escherichia coli* MC1061 was transformed with the reaction mixture, and Ap$^R$ transformants were selected on a bouillon plate containing 100 μg/ml ampicillin. The thus obtained Ap$^3$ strains were examined for plasmids having the desired size and structure. FIG. 5 shows the procedure.

In this manner, pYK268 was obtained from pYK264 and pMC1403; pYK267 from pYK278 and pMC1403; and pYK269 from pYK266 and pMC1403. FIG. 6 shows the base sequences in the junction between plasmid pMC1403 and one of the Psi iso-vectors and the restriction map of the plasmids. By this modification, a BamHI site was added to Psi iso-vectors as a new cloning site. Strains containing the plasmids pYK267, pYK268 and pYK269 have also been deposited with the Fermentation Research Institute as FERM P-6652, 6651 and 6653, respectively and have been transferred to the NRRL under the Budapest Treaty as NRRL B-15561, 15560 and 15562.

EXAMPLE 4

In this example, the lac Z gene (structural gene of B-galactosidase of *Escherichia coli* lackingN-terminal 8 amino acids) on pYK267, 268 and 269 is ligated just after the promoter and the signal sequence of phoA in Example 3. The lac Z gene must be expressed by one of the three plasmids under the control of phosphate. The expression was observed on medium 121 plate containing X-gal. *Escherichia coli* MC1061 (Δlac Z) transformed with the said three plasmids were smeared on the plate and cultured at 37° C. for one day. Blue colonies were formed only by transformants with plasmid pYK269.

Then, *Escherichia coli* MC1061 containing these three plasmids were cultured on medium 121 (−P medium) and medium 121 supplemented with 1 mM phosphate (+P medium) at 30° C. overnight, and the resulting cells were harvested and washed with 50 mM Tris-HCl (pH 8.0). The washed cells were suspended in 20 μl of a buffer solution [5% glycerol, 1% sodium dodecylsulfate, 5% 2-mercaptoethanol, and 0.0625 M Tris-HCl (pH 6.8)]and then heated at 100° C. for 50 seconds to rupture the cells.

Then, 20 μl of the extract was subjected to SDS-polyacrylamide gel electrophoresis [U.K. Laemmli, Nature 227 680-685 (1970)](electrophoresis conditions: 2.5% acrylamide gel, 0.1% SDS, 16 cm×14 cm×0.1 cm, the electrophoresis was conducted at a constant current of 20mA in the concentration gel and at 30 mA after a marker dye was entered in the separation gel). The gel was stained with 0.05% Coomassie Brilliant Blue R 250 (Sigma Co.) to detect protein according to the procedure of G. Fairebanks et al, Biochemistry 10, 2606–2617 (1971), and the results are shown in FIGS. 7 and 8.

Figure 7:
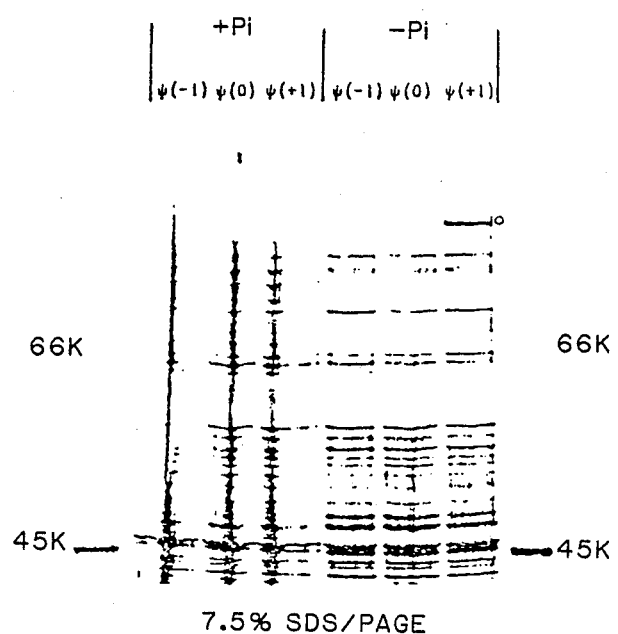
FIG. 7 illustrates the expression of phoA'- lac'Z fusion, wherein "+Pi" shows the addition of 1 mM phosphate, "−Pi" the absence of phosphate, $\psi(-1)$, (0) and (+1) reading frames (−1), (0) and (+1) respectively, and K the molecular weight of $10^3$.
Figure 8:
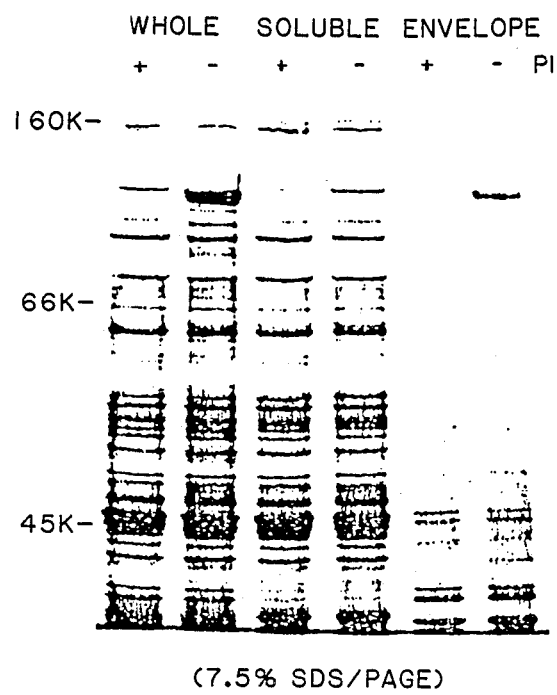
FIG. 8 illustrates the intracellular distribution of phoA'- lac'Z protein, wherein "whole" shows the total extract, "soluble" soluble fractions, "envelope" the distribution in the envelope, "+" the addition of 1 mM phosphate, and "−" the absence of phosphate.

As is apparent from FIG. 7, only the pYK269 plasmid having the reading frame "+1" could express a protein having a molecular weight of about $120 \times 10^3$ (indicated by circle) under phosphate depletion. Most of the 120 K proteins were in the envelope, and it seems that they have gone through a process of partial or complete secretion. (see FIG. 8).

What is claimed is:

1. A microorganism harboring an expression vector selected from the group consisting of pYK264, pYK278, pYK266, pYK268, pYK267 and pYK269

2. An expression vector selected from the group consisting of pYK264, pYK278, pYK268, 2YK267, pYK269 and pYK266.

3. A process for expressing a protein which comprises inserting a structural gene which codes for said protein into a restriction site of an expression vector according to claim 2, transforming an *Escherichia coli* host with said vector, and culturing the transformed *Escherichia coli* under conditions which permit expression of the protein.

* * * * *